United States Patent
Olson, Jr. et al.

(10) Patent No.: US 7,901,407 B2
(45) Date of Patent: Mar. 8, 2011

(54) MEDIA DELIVERY DEVICE FOR BONE STRUCTURES

(75) Inventors: Stanley W. Olson, Jr., San Ramon, CA (US); Lex P. Jansen, Pleasanton, CA (US); Michael Burns, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1654 days.

(21) Appl. No.: 10/211,492

(22) Filed: Aug. 2, 2002

(65) Prior Publication Data
US 2004/0024410 A1   Feb. 5, 2004

(51) Int. Cl.
*A61F 2/46* (2006.01)
(52) U.S. Cl. .......................... 606/86 R; 606/92
(58) Field of Classification Search ............... 606/86, 606/92–94, 105, 79, 82–85, 39, 41, 45, 169, 606/170; 623/17.11–17.16; 206/571; 600/433–435, 600/466, 585; D24/112; 604/164.13, 22
See application file for complete search history.

(56) References Cited

U.S. PATENT DOCUMENTS

| | | | |
|---|---|---|---|
| 2,990,616 A * | 7/1961 | Kuris et al. ................ 433/119 |
| 3,526,219 A * | 9/1970 | Balamuth .................... 600/565 |
| 3,921,044 A * | 11/1975 | McShirley .................. 318/114 |
| 4,445,509 A * | 5/1984 | Auth ............................ 606/159 |
| 4,969,888 A | 11/1990 | Scholten et al. |
| 4,990,134 A * | 2/1991 | Auth ............................ 604/22 |
| 5,051,482 A | 9/1991 | Tepic |
| 5,057,112 A * | 10/1991 | Sherman et al. ............. 606/79 |
| 5,095,915 A * | 3/1992 | Engelson ................... 600/585 |
| 5,108,404 A | 4/1992 | Scholten et al. |
| 5,151,099 A * | 9/1992 | Young et al. ................ 606/27 |
| 5,243,997 A * | 9/1993 | Uflacker et al. ........... 600/585 |
| 5,290,291 A * | 3/1994 | Linden ........................ 606/99 |
| 5,368,595 A * | 11/1994 | Lewis ......................... 606/151 |
| 5,380,329 A * | 1/1995 | Elia et al. .................... 606/72 |
| 5,423,829 A * | 6/1995 | Pham et al. ................ 606/108 |
| 5,443,182 A | 8/1995 | Tanaka et al. |
| 5,545,460 A | 8/1996 | Tanaka et al. |
| 5,569,264 A * | 10/1996 | Tamminmaki et al. ...... 606/104 |
| 5,584,814 A * | 12/1996 | Schuster et al. ............ 604/187 |
| 5,713,906 A * | 2/1998 | Grothues-Spork et al. .... 606/99 |
| 5,718,707 A | 2/1998 | Mikhail |
| 5,722,402 A | 3/1998 | Swanson et al. |
| 5,766,190 A | 6/1998 | Wulfman |

(Continued)

FOREIGN PATENT DOCUMENTS
EP   1 060 731 A1   12/2000
(Continued)

*Primary Examiner* — Thomas C Barrett
*Assistant Examiner* — Nicholas Woodall
(74) *Attorney, Agent, or Firm* — Vista IP Law Group LLP (57) ABSTRACT

Apparatus for delivering a media to an anatomic void within a bone structure and compacting the media within the anatomic void includes a delivery device and a compaction device. The delivery device includes a tubular element, a guidewire, and a removal element. The removal element is capable of forming a void at a target site within the bone structure by cutting and/or deforming target bone tissue. A distal end of the guidewire may be detachable as a safety feature. The compaction device includes an elongate member and a vibration device connected to the proximal end of the elongate member. The vibration device creates vibration at the distal end of the elongate member, so that the media is mixed and/or compacted within the anatomic void.

15 Claims, 8 Drawing Sheets

U.S. PATENT DOCUMENTS

| | | | |
|---|---|---|---|
| 5,851,189 A * | 12/1998 | Forber | 600/585 |
| 5,881,732 A * | 3/1999 | Sung et al. | 128/898 |
| 5,925,038 A | 7/1999 | Panescu et al. | |
| 5,925,051 A | 7/1999 | Mikhail | |
| 5,941,251 A | 8/1999 | Panescu et al. | |
| 5,964,797 A * | 10/1999 | Ho | 606/194 |
| 5,980,528 A * | 11/1999 | Salys | 606/99 |
| 6,093,157 A * | 7/2000 | Chandrasekaran | 600/585 |
| 6,149,655 A * | 11/2000 | Constantz et al. | 606/94 |
| 6,171,312 B1 * | 1/2001 | Beaty | 606/80 |
| 6,190,392 B1 * | 2/2001 | Vandewalle et al. | 606/99 |
| 6,214,012 B1 | 4/2001 | Karpman et al. | |
| 6,248,110 B1 * | 6/2001 | Reiley et al. | 606/93 |
| 6,280,456 B1 | 8/2001 | Scribner et al. | |
| 6,340,299 B1 | 1/2002 | Saito | |
| 6,371,972 B1 * | 4/2002 | Wallace et al. | 606/200 |
| 6,391,024 B1 * | 5/2002 | Sun et al. | 606/34 |
| 6,395,007 B1 | 5/2002 | Bhatnagar et al. | |
| 6,397,850 B1 * | 6/2002 | Scheldrup et al. | 128/899 |
| 6,440,138 B1 * | 8/2002 | Reiley et al. | 606/79 |
| 6,443,988 B2 * | 9/2002 | Felt et al. | 623/17.12 |
| 6,607,478 B2 * | 8/2003 | Williams | 600/3 |
| 6,613,018 B2 * | 9/2003 | Bagga et al. | 604/187 |
| 6,620,162 B2 * | 9/2003 | Kuslich et al. | 606/53 |
| 6,620,185 B1 * | 9/2003 | Harvie et al. | 606/232 |
| 6,730,095 B2 * | 5/2004 | Olson et al. | 606/93 |
| 6,746,451 B2 * | 6/2004 | Middleton et al. | 606/79 |
| 6,824,550 B1 * | 11/2004 | Noriega et al. | 606/159 |
| 6,869,439 B2 * | 3/2005 | White et al. | 606/169 |
| 6,884,264 B2 * | 4/2005 | Spiegelberg et al. | 623/22.12 |
| 6,899,715 B1 * | 5/2005 | Beaty | 606/80 |
| 7,128,746 B2 * | 10/2006 | Singer et al. | 606/90 |
| 2001/0034527 A1 | 10/2001 | Scribner et al. | |
| 2002/0016583 A1 | 2/2002 | Cragg | |
| 2002/0049449 A1 | 4/2002 | Bhatnagar et al. | |
| 2003/0212426 A1 | 11/2003 | Olson, Jr. et al. | |
| 2004/0006347 A1 * | 1/2004 | Sproul | 606/92 |

FOREIGN PATENT DOCUMENTS

| | | |
|---|---|---|
| WO | WO 02/069817 A1 | 9/2002 |

* cited by examiner

MEDIA DELIVERY DEVICE FOR BONE STRUCTURES

BACKGROUND OF THE INVENTION

1. Field of the Invention

The field of the invention pertains to medical devices employed to deliver a media to an anatomic void and, more particularly, to medical devices and methods for delivering a media to a void within a bone structure.

2. Background of the Invention

Spinal injuries, bone diseases such as osteoporosis, vertebral hemangiomas, multiple myeloma, necorotic lesions (Kummel's Disease, Avascular Necrosis), and metastatic disease, or other conditions can cause painful collapse of vertebral bodies. Osteoporosis is a systemic, progressive and chronic disease that is usually characterized by low bone mineral density, deterioration of bony architecture, and reduced overall bone strength. Vertebral body compression fractures (VCF) are common in patients who suffer from these medical conditions, often resulting in pain, compromises to activities of daily living, and even prolonged disability.

On some occasions, VCFs may be repaired by vertebroplasty and other spinal reconstructive means. Vertebroplasty procedures have been used to treat pain and progressive deterioration associated with VCF. Most often in this vertebroplasty procedure, a bone cement, such as polymethylmethacrylate (PMMA), or other suitable biomaterial, is injected percutaneously into the bony architecture under image guidance, navigation and controls. The hardening (polymerization) of the cement media and/or the mechanical interlocking of the biomaterials within the media serve to buttress the bony vault of the vertebral body, providing both increased structural integrity and decreased pain associated with micromotion and progressive collapse of the vertebrae.

Recently, it is more common to treat weakened sites in bones by embedding artificial prosthetic material or prosthetic filler in the weakened sites of the bones or in a mechanically created void within a bone structure. The prosthetic material or prosthetic filler is typically delivered to the void in the form of a fluid media, which hardens or polymerizes after a given period.

Figure 1:
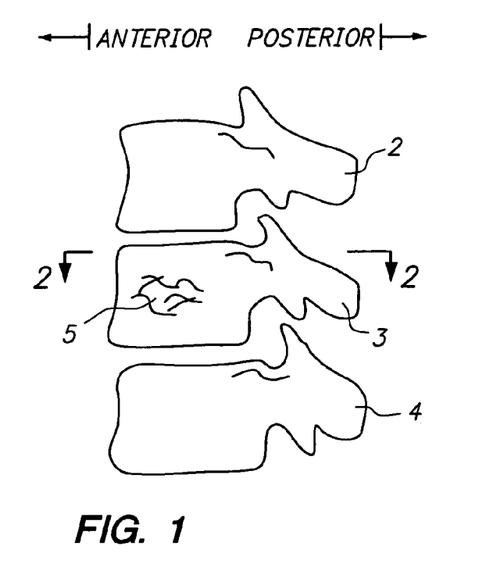
FIG. 1 is a lateral view of three vertebrae, wherein the vertebral body of the middle vertebra has a weakened site.
Figure 2A:
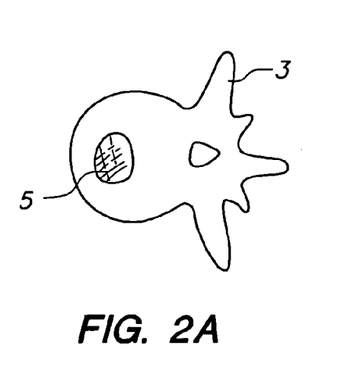
FIG. 2A is a top sectional view of the middle vertebra of FIG. 1.
Figure 2B:
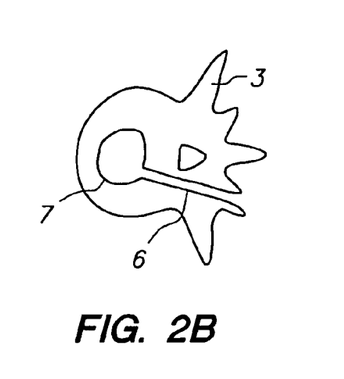
FIG. 2B is a top sectional view of the middle vertebra of FIG. 1, particularly showing a channel and a void created at the vertebra.

Bone tamps (bone balloons or Kyphoplasty™), a balloon-assisted procedure for treatment of VCF or other conditions, also involves injection of a bone cement into a mechanically created bone void within a vertebral body. FIG. 1 shows a side view of three vertebrae 2, 3, and 4. Vertebrae 2 and 4 are healthy vertebrae, while vertebra 3 has a weakened site 5 due to, for examples, injury, diseases, or other causes. FIG. 2A shows a cross-sectional top view of the vertebra 3, particularly showing the weakened site 5. In the bone tamp procedure, a channel 6 is first created that leads to the target site 5. A balloon tamp is then inserted into the structurally compromised vertebral body at the weakened site 5 through the channel 6. A high-pressure balloon is inflated at the target site 5, such that target bone tissues at the target site 5 are pressed against adjacent healthy bone tissues. Some claim that expanding balloon disrupts the target bone tissue and the physiological matrix circumferentially, and directs the attendant bony debris and physiologic matrix towards the inner cortex of the vertebral body vault. As a result, a void 7 at the target site 5 is created. (FIG. 2B) The balloon tamp is then collapsed and removed, leaving the void 7 within the vertebral body of the vertebra 3. Filling it with an appropriate biomaterial media, such as a bone cement, then repairs the void 7.

The balloon tamp procedure is typically performed using multiple components. For example, U.S. Pat. No. 6,248,110 B1 describes a multiple component system for creating a channel at a vertebra using a stylus, a stylet, a guide pin, a trocar, an outer guide sheath, and a drill bit. Multiple component system may be difficult to use and may be expensive.

The use of an expandable balloon tamp to create the anatomic void 7 at the target site 5 may not be possible or the most desirable in certain clinical situations. In particular, because expandable balloon has a fixed geometry and a stretch limit, it may not be the best tool for removing bone tissues precisely or for creating a desired void that has an irregular geometry.

Also, filler material for the bone may not develop its intended strength due to a variety of factors. For example, inadequate or sub-optimal mechanical interlocking of the particles or granules within the physiologic matrices or biomaterial media may result in a weaker tissue and biomaterial construct. Also, excessive voids or void distribution within the biomaterials or bone cement media may result in a construct having inadequate strength.

SUMMARY OF THE INVENTION

In accordance with a first aspect of the invention, apparatus for delivering a media to a target site within a bone structure is provided. In one embodiment, the delivery apparatus includes a tubular element, a guidewire positionable in the tubular element, and a removal element carried by the distal end of the guidewire. The delivery apparatus may further include a handle secured to the proximal end of the guidewire. The distal tip of the tubular element is preferably sharpened and is preferably made of a material having sufficient toughness so as to facilitate the insertion of the tubular element into the bone structure, and the creation of a channel in the bone structure that leads to the target site. The tubular element may also be used to deliver the media to the anatomic void within the bone structure. Alternatively, an inner tubular element, coaxially positioned within the tubular element, may be used to deliver the media to the anatomic void.

Preferably, the distal end of the guidewire assumes a low profile when residing within the lumen of the tubular element, and assumes a relaxed non-linear configuration when it is unconstrained outside the tubular element. The distal end of the guidewire can be made of a radiopaque material so that the orientation and/or position of the guidewire can be determined using a fluoroscope. Alternatively, an operative element, such as an electrode, may be carried on the distal end of the guidewire for navigation purposes using a signal sensing system. The electrode may also be used for ablation of bone tissue for lesion generation in a bony structure. As a further alternative, a marker located at the proximal end of the guidewire, or at the handle, is provided for indicating the orientation of the distal end of the guidewire.

The removal element reaches the target site through the channel, and creates an anatomic void at the target site within the bone structure, e.g., by cutting and/or deforming target bone tissue. The removal element can preferably be steered by manipulating the proximal end of the guidewire. In one embodiment, the removal element includes a tip that is a part of, or separately connected to, the distal end of the guidewire. Alternatively, the removal element may include a bead, a burr, or an expandable structure for cutting a bone tissue. In an alternate embodiment, pressurized gas, such as an inert gas, delivered by an inner tubular element coaxially positioned within the tubular element is used to create the void at the target site. In this case, a guidewire is not required. The distal end of the inner tubular element may have a linear or non-linear relaxed configuration.

The distal end of the guidewire may be detachable from the rest of the guidewire for safety purposes. In this case, the distal end of the guidewire and/or the removal element may be made from a bio-compatible material, so that it may be readily detached from the proximal portion of the guidewire and left in the void together with the filler biomaterial. In one embodiment, the distal end of the guidewire is connected to the proximal portion of the guidewire by a sacrificial link that could be severed by an electrolytic detachment mechanism. In another embodiment, the distal end of the guidewire is detachably secured to the proximal portion of the guidewire by a screw mechanism. In yet another embodiment, a portion of the guidewire connecting the distal end is removed to create a link, which could be severed by pulling or rotating the proximal end of the guidewire.

In accordance with a further aspect of the invention, the delivery apparatus may include a vibration device that is connected to the proximal end of the guidewire for causing vibration at the distal tip of the guidewire. Vibration at the distal tip of the guidewire mobilizes the particles or granules within the media, creating liquefaction of the media, and rearranges the particles or granules so that they mechanically interlock or interdigitate with one another to form a more stable construct. If desired, after a first compaction, the distal tip of the guidewire may be reintroduced into the media to re-mobilize the particles or granules within the media, causing liquefaction and re-compaction of the media. This may be particularly advantageous when the operator prefers an alternate distribution of the biomaterial media within the bony vault.

In one embodiment, a compaction device for compacting a media within an anatomic void is provided. The compaction device includes a vibration device coupled to an elongate member. During operation, the vibration device causes the elongate member to vibrate at a frequency. The distal end of the elongate member may be linear, or alternatively, may assume a non-linear relaxed configuration. The compaction device may further include a least one operative element, e.g., an electrode, carried on the distal end of the elongate member for navigation purposes and/or ablation of body tissue. The compaction device may also include a handle coupled to the proximal end of the elongate member for manipulating the distal end. A marker may be provided on the proximal end of the elongate member or on the handle for indicating the orientation of the distal end of the elongate member. The elongate member distal end may carry a sensor for measuring a characteristic of the media. Based at least on the measured characteristic, the frequency of vibration can then be automatically set or manually adjusted.

Methods of using the delivery device and/or the compaction device are also described herein. Other and further aspects and features of the invention will be evident from reading the following detailed description of the preferred embodiments, which are intended to illustrate, and not limit, the invention.

BRIEF DESCRIPTION OF THE DRAWINGS

The drawings illustrate the design and utility of preferred embodiments of the invention, in which similar elements are referred to by common reference numerals. In order to better appreciate how the above-recited and other advantages and objects of the invention are obtained, a more particular description of the invention briefly described above will be rendered by reference to specific embodiments thereof, which are illustrated in the accompanying drawings. It will be understood that these drawings depict embodiments of the invention, and are not to be considered limiting of its scope, the invention will be described and explained with additional specificity and detail through the use of the accompanying drawings in which.

DETAILED DESCRIPTION OF THE PREFERRED EMBODIMENTS

Figure 3:
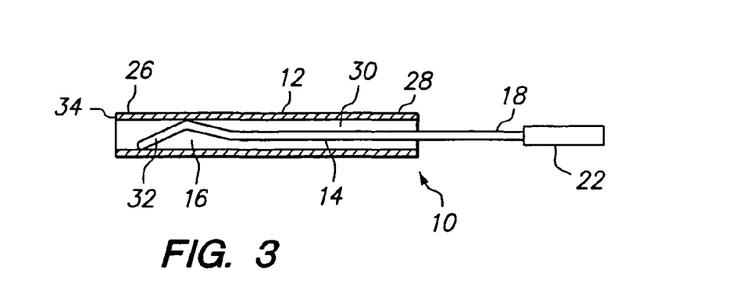
FIG. 3 is a cross-sectional side view of a delivery device constructed in accordance the first preferred embodiment of the invention, particularly showing the distal end of the guidewire within the tubular element.

FIG. 3 shows a side view of a delivery device 10 in accordance with a first preferred embodiment of the invention. The delivery device 10, which is capable of creating a void in an object, such as a bone structure, includes a tubular element 12, and a guidewire 14 having a distal end 16 and a proximal end 18. The tubular element 12 has a distal end 26, a proximal end 28, and a lumen 30 extending between the proximal end 28 and the distal end 26. The guidewire 14 is coaxially positioned in the lumen 30 of the tubular element 12 and is capable of being advanced or retracted coaxially within the lumen 30 of the tubular element 12. The delivery device 10 also includes a removal element 32 carried on the distal end of the guidewire 14. The removal element 32 will be described in further details below. Although not required, the delivery device 10 may also include a handle 22 coupled to the proximal end 18 of the guidewire 14.

The tubular element 12 is preferably a catheter or a microcatheter. Alternatively, the tubular element 12 may be a sheath, introducer, or any tube, and may be made of a variety of materials, including, but not limited to, plastics, metals, and polymers. The tubular element 12 may be flexible so that it is capable of winding through a tortuous path that leads to the target site. Alternatively, the tubular element 12 may be made stiff, i.e., by being made of a stiff material, or by being reinforced with a coating or a coil, to control the amount of flexing. The stiffness or flexibility of the tubular element 12 is a matter of design choice, and it depends on the particular application. The outer diameter of the tubular element 12 is preferably less than ½ inch. However, other dimensions for the outer diameter of the tubular element 12 may also be appropriate, depending on the particular application or clinical procedure. The tubular element 12 should have an inner diameter so as to allow the guidewire 14 to be advanced and retracted within the lumen 30 of the tubular element 12. In addition, the inner diameter of the tubular element 12 should be wide enough to allow a media to be delivered within the lumen 30 of the tubular element 12. Alternatively, a second tubular element may deliver the media, and the tubular element 12 should have an inner diameter wide enough such that the second tubular element can be coaxially positioned within the lumen 30 of the tubular element 12.

Figure 3A:
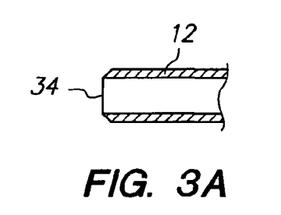
FIGS. 3A to 3C are partial cross-sectional side views of variations of the distal end of the tubular element.
Figure 3B:
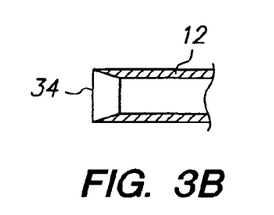
Figure 3C:
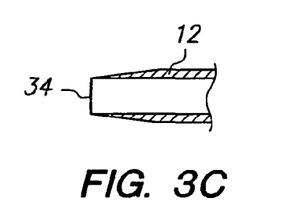

The distal tip 34 of the tubular element 12 shown in FIG. 3 is blunt. If the thickness or cross-sectional profile of the wall of the tubular element 12 is small, the distal tip 34 of the tubular element 12 could be used as a cutting or deforming tool for boring or coring a bone structure. In this case, the distal end of the tubular element 12 is preferably made of a tough material, such as steel or other alloys, so that it could penetrate a bone structure without being damaged. Alternatively, the distal tip 34 of the tubular element 12 may be advantageously sharpened or wedged as illustrated in FIGS. 3A-3C. In FIG. 3A, the outer surface of the wall at the distal tip of the tubular element 12 is tapered to create a low cross-sectional profile of the wall. In FIG. 3B, the inner surface of the wall at the distal tip of the tubular element 12 is tapered to create a low cross-sectional profile of the wall. FIG. 3C shows a cross-sectional profile of the wall of the tubular element 12 in which both the outer surface and the inner surface of the wall at the distal tip of the tubular element 12 are tapered. The sharp distal tip 34 of the tubular element 12 facilitates the insertion of the tubular element 12 into a bone structure, and boring of the bone structure. An advantage of having a tubular element 12 that could perform both the boring of a bone structure and delivery of a media is that it reduces the number of components typically required in a treatment procedure.

The guidewire 14 preferably has a circular cross-sectional shape. Alternatively, the guidewire 14 may have other geometric cross-sectional shapes, such as oval, rectangle, and triangle, or other random shapes. The materials used in constructing the guidewire 14 may comprise any of a wide variety of materials, such as plastics, nitinol, titanium, and alloys. In a preferred embodiment, a radiopaque material such as a metal (e.g., stainless steel, titanium alloys, or cobalt-chrome alloys) is used. Alternatively, a polymer, such as an ultra high molecular weight polyethylene, may also be used to construct the guidewire 14. In another preferred embodiment, where it is desirable to leave a portion of the guidewire 14 implanted in a patient, a bioabsorbable material may be used. These include, but are not limited to, polylactic acid (PLA) and polyglycolic acid (PGA). Alternatively, a biocompatible material, such as polymethylmethacrylate (PMMA) may be used to form the distal end 16 of the guidewire 14. A combination of materials may also be used. For example, a bioabsorable material, such as PLA may be used to make the distal end 16 of the guidewire 14, and a metal, such as stainless steel, may be used to construct the proximal portion of the guidewire 14. Detachable distal end 16 of the guidewire 14 will be discussed in further details below. It should be noted that the stiffness of the guidewire 14, being a function of the diameter of the guidewire 14 and the material from which the guidewire 14 is made of, is preferably selected so that the guidewire 14 is stiff enough to cut, deform, and/or compact target bone tissue.

Figure 4:
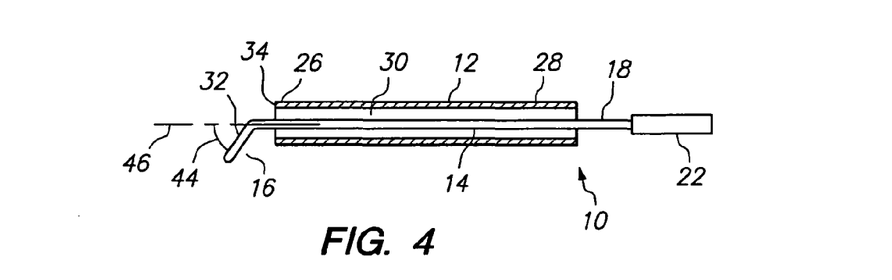
FIG. 4 is a cross-sectional side view of the delivery device of FIG. 3, particularly showing the distal end of the guidewire outside the lumen of the tubular element.
Figure 5A:
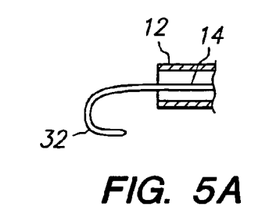
FIGS. 5A to 5C are variations of the distal end of the guidewire, particularly showing different relaxed configurations of the guidewire.
Figure 5B:
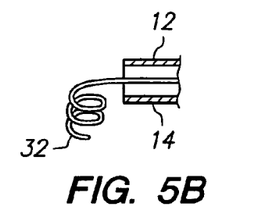
Figure 5C:
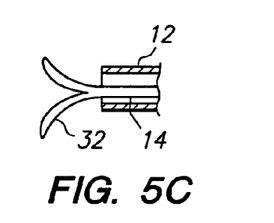

As shown in FIG. 3, when the distal end 16 of the guidewire 14 is coaxially positioned within the lumen 30 of the tubular element 12, the distal end 16 is stretched or bent into a second configuration that has a relatively small cross sectional profile such that the distal end 16 can fit within the lumen 30 of the tubular element 12. The distal end 16 of the guidewire 14 resumes its relaxed configuration 42 when the distal end 16 is positioned distal to the distal end 26 of the tubular element 12 such that the distal end 16 is unconstrained by the tubular element 12. (FIG. 4) As shown in FIG. 4, the distal end 16 of the guidewire 14 is bent or preformed such that the distal end 16 forms an angle 44 with an axis 46 of the guidewire. Alternatively, the distal end 16 of the guidewire 14 may be bent or preformed into other shapes, such as a curvilinear geometry or a spiral. FIGS. 5A to 5C shows several examples of the shape of the distal end 16 of the guidewire 14. FIG. 5A shows the distal end 16 of the guidewire 14 having a curvilinear shape. FIG. 5B shows the distal end 16 of the guidewire 14 having a spiral shape. FIG. 5C shows the distal end 16 of the guidewire 14 having a dual-curvilinear shape.

Figure 6A:
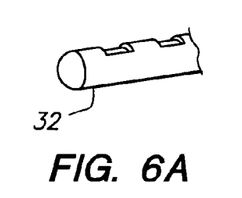
FIGS. 6A to 6D are different designs of the distal end of the guidewire.
Figure 6B:
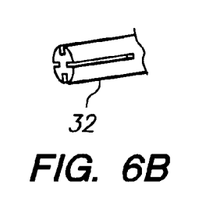
Figure 6C:
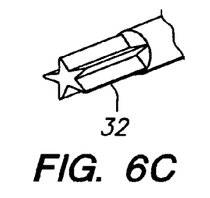
Figure 6D:
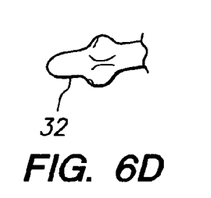

Returning to FIG. 3, the removal element 32 is a portion of the distal end 16 of the guidewire 14, which could be positioned by manipulating the proximal end 18 of the guidewire 14. The removal element 32 may include abrasive particles, such as diamond dusts, deposited at the surface of the distal end 16 of the guidewire 14, for cutting, digging, and/or abrading against target bone tissue. Alternatively, the removal element 32 may be formed by sharpening or removing a portion of the distal end 16 of the guidewire 14, such as those shown in FIGS. 6A to 6C, or by deforming a portion of the distal end 16 of the guidewire 14, such as those shown in FIG. 6D. As a further alternative, the removal element 32 may be separately fabricated apart from the guidewire 14 and is then secured to the distal end of the guidewire 14 by a connection such as a weld, brazing, or glue, depending on the material from which the removal element 32 and the guidewire 14 is made. The removal element 32 is not limited to the foregoing examples, and may have a variety of shapes and sizes, so long as the removal element 32 is capable of cutting, deforming, and/or pushing a target bone tissue against an adjacent tissue that is intended to be preserved.

Figure 7:
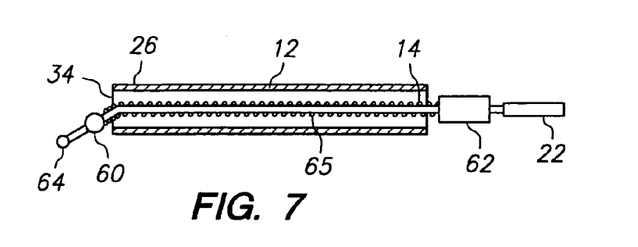
FIG. 7 is a cross-sectional side view of an alternative embodiment of the device of FIG. 3, particularly showing a variation of the removal element having a bead.

FIG. 7 shows another variation of the removal element 32. The removal element 32 includes a bead 60 for cutting and/or drilling purpose. The bead 60 is connected to a motor 62 by a drive shaft 64, which coaxially surrounds the guidewire 14. The motor 62 causes the bead 60 to rotate about the guidewire 14, and the rotating bead 60 is then used as a tool for cutting bone tissue. The bead is preferably covered by sharp particles, such as diamond dusts, thereby forming a burr. Alternatively, portion(s) of the bead 60 may be cut or deformed to form sharp edges on the surface of the bead 60 for cutting, sanding, and/or drilling purposes. The distal end 16 of the guidewire 14 may be bent or preformed into a variety of shapes so that the guidewire 14 could be used for guiding the bead 60 through a non-linear path. In particular, the bead 60 can be guided along the distal end 16 of the guidewire 14 by advancing or retracting the bead 60 relative to the guidewire 14. The bead 60, together with the distal end 16 of the guidewire 14, may be navigated and turned relative to the distal tip 34 of the tubular element 12 by manipulating the proximal end of the guidewire 14 in a torsional and/or axial direction. Furthermore, the bead 60 may be advanced or retracted relative to the tubular element 12 by positioning the proximal end 18 of the guidewire (or the handle 22 if one is provided) relative to the tubular element 12. A tip 64 located at the distal tip of the guidewire 14 is used to prevent the bead 60 from being distally advanced too far. Similar drilling devices are described in the U.S. Pat. No. 4,990,134, the entire of which is incorporated by reference herein.

Figure 8A:
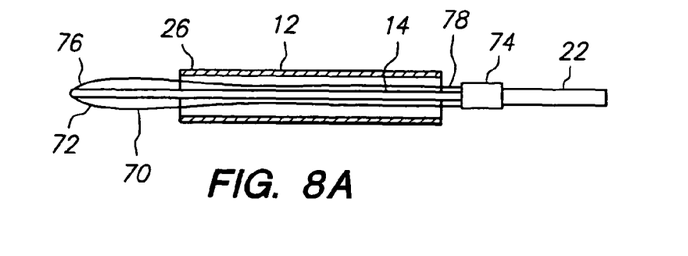
FIG. 8A is a cross-sectional side view of an alternative embodiment of the device of FIG. 3, particularly showing another variation of the removal element having an expandable basket.
Figure 8B:
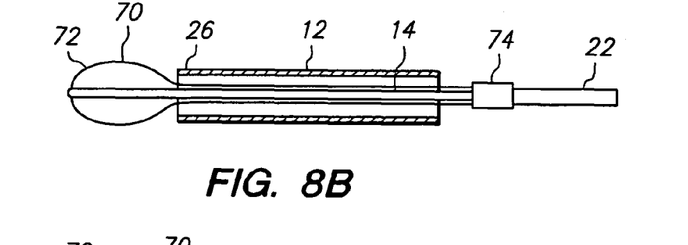
FIG. 8B is a cross-sectional side view of the device of FIG. 8A, particularly showing the expandable basket assuming an expanded profile outside the tubular element.
Figure 8C:
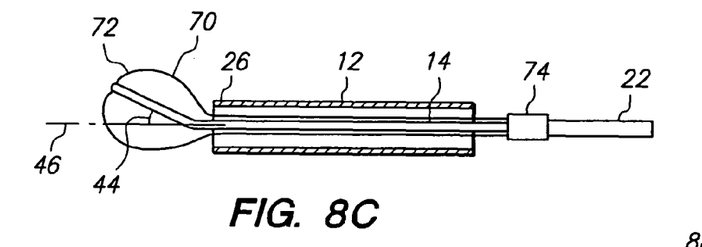
FIG. 8C is a variation of the device of FIG. 8A, particularly showing the distal end of the guidewire having a non-linear configuration.
Figure 8D:
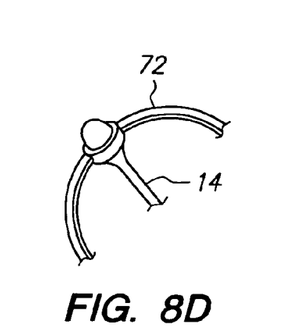
FIG. 8D is an isometric view of the distal end of an expandable basket that is rotatably secured to the distal end of the guidewire.

FIGS. 8A-8C show another variation of the removal element 32, which includes an expandable cutting basket 70. Although the expandable cutting basket 70 is shown to include two flexible wires 72, it may include any number of wires 72. Furthermore, the cutting basket 70 is not necessarily limited to the example illustrated in FIG. 8A. The cutting basket 70 may be, for examples, a braided structure, or an inflatable balloon having sharp particles or granules deposited on its surface. The distal end of the cutting basket may be secured to the guidewire 14 so that rotating the proximal end of the guidewire 14 will cause rotation of the expandable cutting basket 70. Alternatively, as shown in FIG. 8D, the distal end of the expandable cutting basket 70 may be rotatably secured to the guidewire 14 so that the cutting basket 70 can rotate about the guidewire 14. In either case, the cutting basket 70 may be rotated manually or by a machine.

As shown in FIGS. 8A and 8B, the cutting basket assumes a low profile while residing within the lumen 30 of the tubular element 12, and is free to assume an expanded profile when it is unconstrained outside the tubular element 12. The cutting basket may be self-expanding or self-collapsing. Self-expanding basket has a relaxed expanded configuration, and may be collapsed by positioning the opposite ends 76 and 78 of the wires 72 (or the elements defining the cutting basket 70) further from one another. Self-collapsing basket has a relaxed collapsed (or unexpanded) configuration, and may be expanded by positioning the opposite ends 76 and 78 of the wires 72 (or the elements defining the cutting basket 70) closer towards one another. The shape of the cutting basket may be changed, for example, by varying the tension or compression on any or all of the wires 72 via a control 74. FIGS. 8A and 8B show that the guidewire 14 is substantially linear. Alternatively, as shown in FIG. 8C, the distal end 16 of the guidewire 14 may be bent or preformed such that it forms an angle 44 with an axis 46 of the guidewire 14. Expandable structures are described in U.S. Pat. No. 5,925,038, the entirety of which is incorporated by reference herein.

Figure 9A:
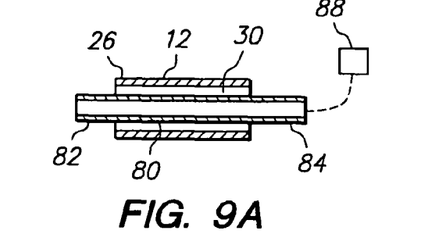
FIG. 9A is a cross-sectional side view of an alternative embodiment of the device of FIG. 3, particularly showing an inner tubular element coaxially positioned within the tubular element for delivery of a pressurized gas.
Figure 9B:
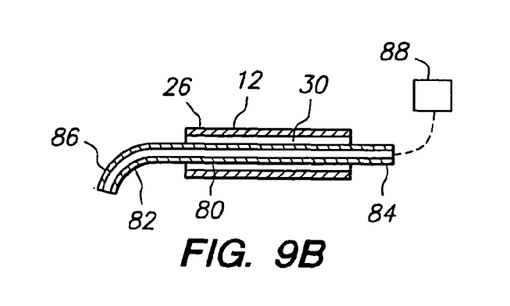
FIG. 9B is a cross-sectional side view of a variation of the device of FIG. 9A, particularly showing the inner tubular element having a non-linear distal end.

FIG. 9A shows another variation of the removal element 32 that does not require a guidewire. As shown in FIG. 9A, the removal element 32 includes a second tubular element 80 coaxially secured within the tubular element 12. The second tubular element 80 has a distal end 82 adapted to be placed within an anatomic void, and a proximal end 84 adapted to be coupled to a media supply 88. The second tubular element 80 delivers from the supply 88, a media, preferably an inert gas or $CO_2$, under high pressure in order to deform target bone tissue. The distal end 82 of the second tubular element 80 may have a linear relaxed configuration, as shown in FIG. 9A. Alternatively, the distal end 82 of the second tubular element 80 may assume a non-linear configuration 86 when it is unconstrained outside the lumen 30 of the tubular element 12, and is stretched to a second configuration having a lower profile when it is within the lumen 30 of the tubular element 12. (FIG. 9B)

It should be noted that the removal element 32 is not limited to the embodiments described herein, and that other variations of the removal element 32, such as an expandable balloon, may also be used so long as the removal element is capable of creating a void within a bone structure by cutting and/or deforming target bone tissue. Furthermore, as illustrated in the previous examples, the removal element 32 is preferably capable of creating a void that has a larger profile than the cross-sectional dimension of the tubular element 12.

Figures 10A, 10B:
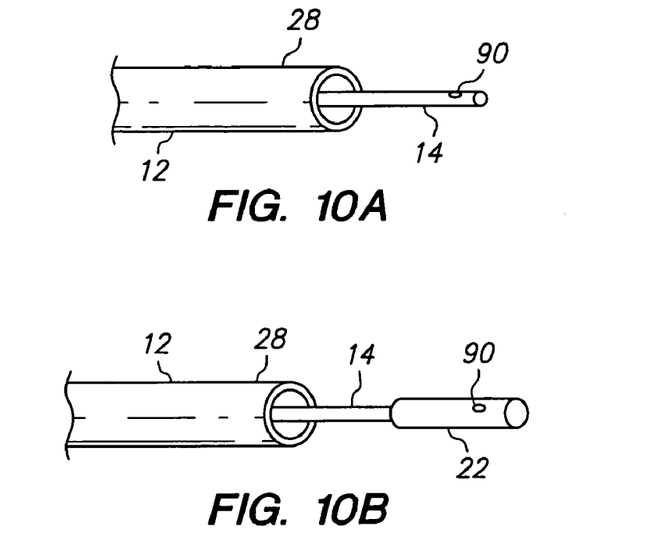
FIG. 10A shows a proximal end of the guidewire of FIG. 3, particularly showing the marker located at the proximal end of the guidewire.
FIGS. 10B and 10C each shows the handle of the device of FIG. 3, particularly showing the marker located at the proximal end of the handle.
Figure 10C:
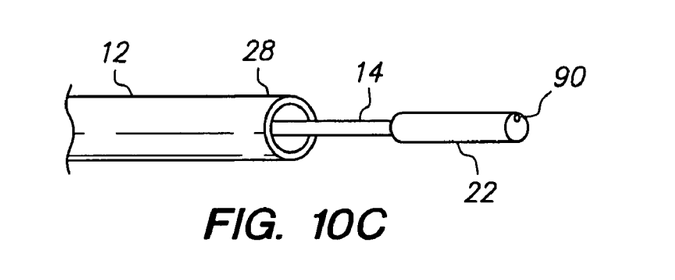
Figure 10D:
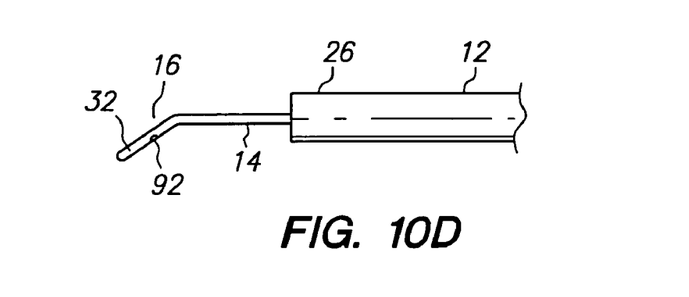
FIG. 10D is a partial side view of the device of FIG. 3, particularly showing an electrode being carried on the distal end of the guidewire.

In any of the above-described embodiments, the device 10 may include a marker 90 located at the proximal end of the guidewire 14 for indicating the orientation of the removal element 32 at the distal end of the guidewire 14. Alternatively, if a handle 22 is provided, the marker 90 may be carried on the handle 22, as shown in FIGS. 10B and 10C. In addition, or alternatively, the distal end 16 of the guidewire 14 may be made of a radiopaque material for indicating the orientation and/or position of the removal element 32. Radiopaque guidewire is described in U.S. Pat. No. 6,093,157, the entirety of which is incorporated by reference herein. Other navigation tools, such as stereotactic guidance, magnetic guidance, endoscopic guidance, and 3-D localization, as are commonly known in the art, may also be used to assist navigation of the distal end 16 of the guidewire 14. Furthermore, as shown in FIG. 10D, the distal end 16 of the guidewire 14 may include at least one operative element 92, such as an electrode, which may be used for navigation purpose and/or for ablation of target bone tissue to create a lesion. Navigation systems using electrode(s) for transmitting and/or receiving a signal have been described in U.S. Pat. Nos. 5,941,251 and 5,722,402, the entirety of which is hereby incorporated by reference.

Any of the devices discussed previously may further include a vibration device for creating compaction of a media. As used in this specification, the term, "compaction" refers to the act of changing the structural arrangement of the elements in the media, such that particles or granules within the media mechanically interlock or interdigitate with each other to form a more stable configuration. During the compaction process, particles and/or granules within the media are mobilized, resulting in liquefaction of the media. The net effect of the compaction is to minimize the size of the voids that may be present within the media so that a construct with a desired porosity can be achieved when the media hardens.

Figure 11:
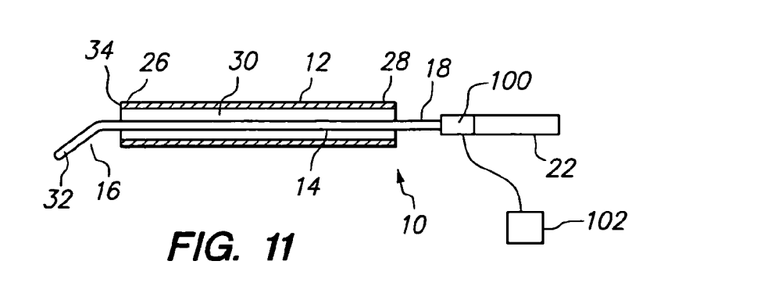
FIG. 11 is a cross-sectional side view of the device of FIG. 3, particularly showing the vibration device coupled to the proximal end of the guidewire.

FIG. 11 shows a side view of the delivery device 10 of FIG. 3, which includes a vibration device 100. The vibration device 100 is mechanically coupled to the proximal end 18 of the guidewire 14. The vibration device 100 is adapted to be coupled to a power source 102, such as an electrical outlet, that is external to the vibration device 100. Alternatively, the power source 102 may be, for example a battery that is internal to the vibration device 100. The vibration device 100 generates vibration to the guidewire 14 at the proximal end 18 of the guidewire, and causes the distal end 16 of the guidewire 14 to vibrate. A handle 22 may be provided that is preferably coupled to the vibration device 100. In this case, the power source 102 may be internal to the handle 22.

The vibration device 100 is mechanically coupled to the proximal end 18 of the guidewire 14, and causes the guidewire 14 to vibrate during operation of the device 10. The vibration device 100 preferably includes a motor for causing the guidewire 14 to vibrate at a frequency. The frequency of vibration is preferably within the range of 1/sec to 200/sec. However, depending on the composition, consistency, density, and/or temperature of the media, and/or the size, density, and/or size distribution of the particles or granules in the media, other ranges of frequency may be used as well. In one embodiment, the frequency of the vibration device 100 can be adjusted by a control (not shown) located at the proximal end 18 of the guidewire 14. Alternatively, the distal end 16 of the guidewire 14 may carry a sensor (not shown) that measures a characteristic, i.e., temperature, of the media, and the frequency of the vibration is then automatically set or manually adjusted based at least on the measurement.

Figure 12A:
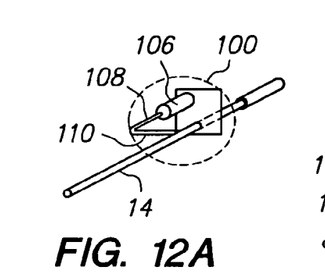
FIGS. 12A to 12C are variations of the vibration device of FIG. 11.
Figures 12B, 12C:
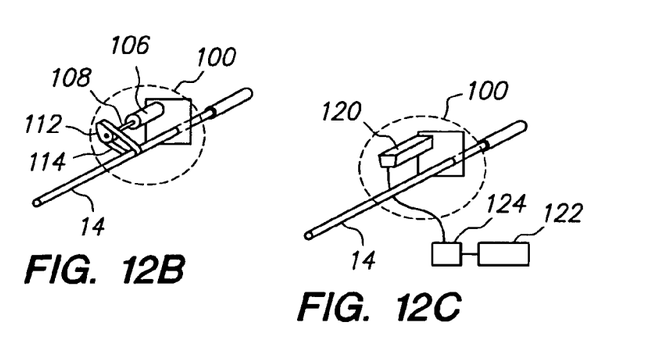

The motor may be a piezoelectric motor, an electric motor, an electromagnetic motor, or an inert gas driven motor. FIGS. 12A-12C illustrates several examples of the vibration device 100.

FIG. 12A shows a vibration device 100 that includes a motor 106 having a shaft 108. The shaft 108 of the motor 106 is connected to an element 110, which is preferably made of a durable material. During operation, the motor 106 causes the element 110 to turn and contact the guidewire 14. As such, the element 110 delivers mechanical energy to the guidewire 14 and causes the guidewire 14 to vibrate.

FIG. 12B shows another variation of the vibration device 100 that also includes a motor 106 having a shaft 108. The shaft 108 of the motor 106 is connected to a disk 112 that has a non-circular geometry. A cable or belt 114 engages the circumference of the disk 112 and a portion of the guidewire 14. During operation, the motor 106 causes the disk 112 to turn. Because the disk 112 is non-circular, the motor 106 causes the cable or belt 114 to exert an alternating pulling force against the guidewire 14, making the guidewire 14 vibrate.

FIG. 12C shows a vibration device 100 that does not require a mechanical motor. The vibration device 100 includes a metal 120 that may be magnetized by an electric current supplied by a power source 122. A control 124, being electrically coupled to the power source 122 and the metal 120, causes the metal 120 to be intermittently magnetized at a desired frequency. The guidewire 14 is made of a metal in this particular example. During operation, the magnetized metal 120 intermittently attracts the metal guidewire 14, causing the guidewire 14 to vibrate.

It should be noted that the vibration device 100 is not limited to the examples discussed above. The vibration device 100 may include any device adapted for, or capable of, delivering energy to the guidewire 14 so as to cause the guidewire 14 to vibrate.

The vibration device 100 is shown in FIGS. 12A-12C to be a part of the delivery device 10. However, as another aspect of the invention, the vibration device 100 may be coupled to an elongate member 130 and forms a compaction device 128 used solely for compacting a media, such as that shown in FIG. 13. The elongate member 130 is preferably made of a metal. However, the elongate member 130 may also be made of other materials, including, but not limited to plastics, nitinol, titanium, methacrylates, and alloys. Also, any of the materials discussed previously in reference to the guidewire 14 of the delivery device 10 is also suitable for construction of the elongate member 130. The elongate member 130 should be made durable enough to sustain vibration within a range of frequencies. The stiffness of the elongate member 130, being a function of the diameter of the elongate member 130 and the material from which the elongate member 130 is made of, is preferably selected so as to produce a desired amplitude of the vibration at the distal tip 132 of the elongate member 130. The elongate member 130 may have a non-linear distal end, such as a J-tip or other shapes. The vibration device may also include an operative element, such as an electrode, carried on the distal end of the elongate member 130 for navigation and/or ablation purpose. Alternatively, or additionally, a marker may be placed at the proximal end of the elongate member 130, or at the handle if one is provided, for indicating the orientation of the distal end of the elongate member 130. The distal end of the elongate member 130 may carry a sensor for measuring a characteristic of the media, and the frequency of vibration is then set, automatically or manually, based at least on the measurement, as discussed previously. Furthermore, the distal end of the elongate member 130 may be detachable from a remainder of the elongate member 130 for safety purpose, as will be described below.

Figure 13:
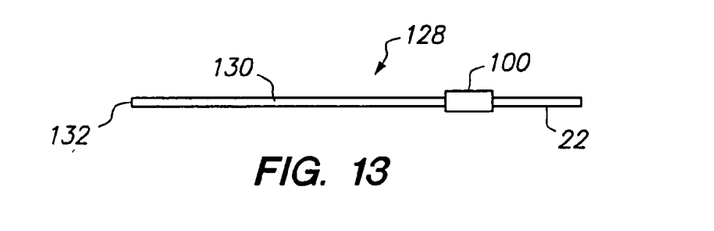
FIG. 13 is a side view of a compaction device in accordance with a second aspect of the invention.

When using the compaction device 128 of FIG. 13 for compaction of a media, the distal tip 132 of the elongate member 130 of the compaction device is first inserted into the media. The vibration device 100 is then activated to cause the distal tip 132 of the elongate member 130 to vibrate for compaction of the media.

It should be appreciated that the compaction device 128 is not limited to compaction of a media within a bone structure, and that it has broad applications in other areas of the body. For example, the compaction device 128 may also be used to compact, liquefy, and/or mix a media within an aneurysm, a vessel, or other body cavities. The compaction device 128 may also be used to compact, liquefy, and/or mix a media contained within a container, such as a balloon or a biomaterial containment device, that is adapted to be placed within a body cavity. Biomaterial containment device has been described in U.S. patent application Ser. No. 10/142,133, filed on May 8, 2002, entitled, "TACTICAL DETACHABLE ANATOMIC CONTAINMENT DEVICE AND THERAPEUTIC TREATMENT SYSTEM," the entirety of which is incorporated by reference herein. The compaction device 128 may also be used to compact and/or liquefy a media outside the body in association with a particular medical treatment, procedure, or experiment. For example, the compaction device 128 may be used to prepare a media to be introduced into a patient. Furthermore, besides using the compaction device 128 in a fluid media, the compaction device 128 may also be used to mobilize solid particles or granules contained in a cavity or a lumen. This is particularly useful in the situation where it is desirable to introduce solid particles or granules through a channel. The compaction device 128 can then be used to mobilize the particles or granules that are clustered and became jammed or immovable in the channel, and facilitates movement of the solid particles or granules through the channel.

Figure 14A:
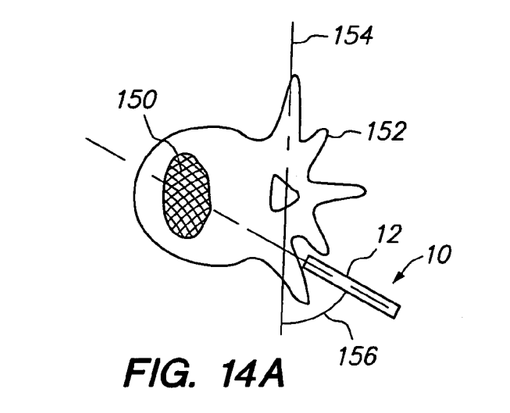
FIGS. 14A to 14F are cross-sectional top views of a vertebra being treated by the device of FIG. 3.

The method of using the delivery device 10 will now be discussed with reference to FIGS. 14A-14F. When using the delivery device 10 to create a void at a target site 150 within a bone structure, such as a vertebra 152, the guidewire 14 is positioned such that the distal end 16 of the guidewire 14 is coaxially surrounded within the distal end 26 of the tubular element 12. Alternatively, the guidewire 14 may be completely removed from the lumen 30 of the tubular element 12. The target site 150 is typically a degenerated area within a bone structure, and tends to be relatively fragile (brittle and/or friable) when compared to the adjacent bone tissues that are intended to be preserved. The tubular element 12 is then used to bore the vertebra 152. As shown in FIG. 14A, the tubular element 12 is positioned at an angle 156 relative to an axis 154 of the vertebra 152 so that a distal advancement of the tubular element 12 would reach the target site 150 of the vertebra 152. FIG. 14A shows the tubular element 12 being inserted into the vertebra 152 at a transpedicular direction.

Figure 14B:
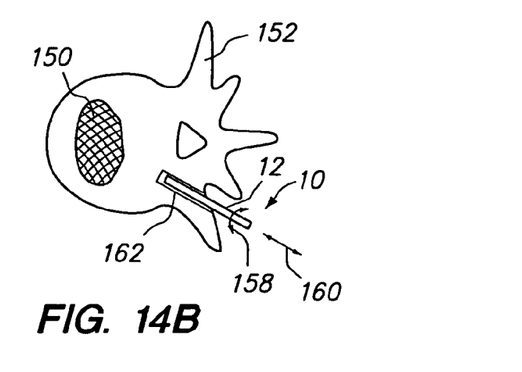

As shown in FIG. 14B, torsional motion, represented by the arrow 158, and/or axial motion, represented by the arrow 160, may be applied to the tubular element 12 to facilitate boring of the vertebra 152. The boring or coring of the vertebra 152 creates a channel 162, which houses the tubular element 12. The torsional motion and the axial motion may be applied manually or mechanically (i.e., by a machine). Furthermore, an object, such as a hammer or a plunger, may be used to tap against the proximal end 28 of the tubular element 12 in order to bore the tubular element 12 into the vertebra 152. Tubular element 12 having sharpened edges, such as those shown in FIGS. 3A-3C, could more efficiently cut or deform bone tissue. Alternatively, a separate device may be used to drill through a portion of the vertebra 152 to create the channel 162. Once the channel 162 leading to the target site 150 is created, the tubular element 12 is then inserted into the channel 162.

After the channel 162 is created and the tubular element 12 is secured within the channel 162, if the guidewire 14 was not initially placed within the lumen 30 of the tubular element 12, the guidewire 14 is then inserted into the lumen 30 of the tubular element 12. When being coaxially surrounded by the tubular element 12, the distal end 16 of the guidewire 14 is stretched or bent into a configuration that has a relatively smaller cross-sectional profile. The guidewire 14 is then advanced distally by manipulating the proximal end 18 of the guidewire 14, or the handle 22, if one is provided. When the distal end 16 of the guidewire 14 exits the lumen 30 of the tubular element 12, it assumes a second profile, e.g., a profile with an expanded configuration. Outside the tubular element 12, the distal end 16 of the guidewire 14 engages or comes in contact with the target bone tissue. (FIG. 14C) Because the guidewire is stiffer than the degenerated tissue at the target site 150, the guidewire 14 cut into the degenerated bone tissue when it emerges from the tubular element 12.

Figure 14C:
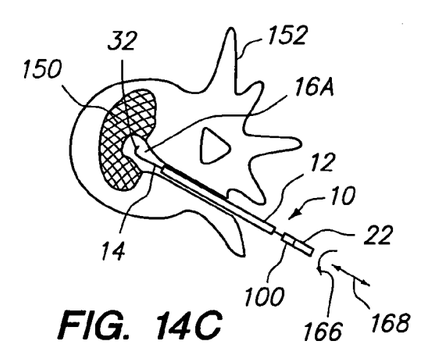
Figure 14D:
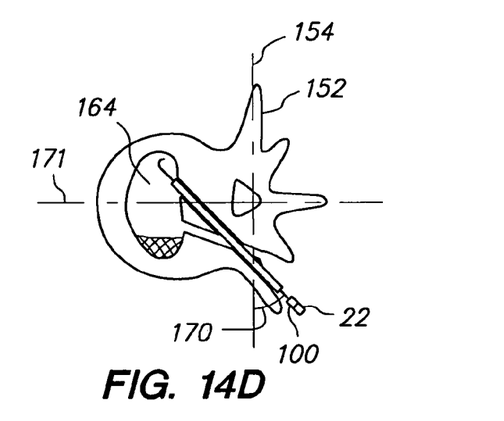
Figure 14E:
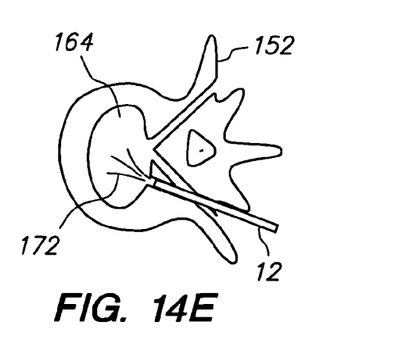
Figure 14F:
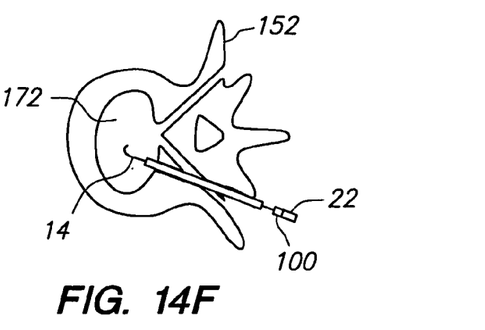

As shown in FIG. 14C, torsional motion, as represented by arrow 166, and axial motion, as represented by arrow 168, may be applied to the proximal end 18 of the guidewire 14, or to the handle 22 if one is provided, so that the removal element 32 at the distal end 16 of the guidewire 14 may engage the target bone tissue at the target site 150. The torsional motion and the axial motion may be applied manually or mechanically (i.e. by a machine). Depending on the configuration and type of the removal element 32, the removal element 32 may cut through the target bone tissue at the target site 150, and/or may deform the target bone tissue by compressing it against the adjacent healthy bone tissue, while the torsional and/or axial motion is being applied to the guidewire 14. When a desired amount of bone tissue is cut or pressed against the adjacent healthy bone tissue, a void 164 is created. A device (not shown) attaching to the proximal end 28 of the tubular element 12 may be used to create suction within the lumen 30 of the tubular element 12 to remove bone tissue matrices during the void-creation process.

If the device 10 includes a bead 60, such as that shown in FIG. 6, the bead 60 may be used to create the channel 162 and the void 164 in the vertebra 152. In this case, the motor 62 causes the bead 60 to rotate about the guidewire 14. The bead 60 may be navigated to the desired target site 150 by rotating and axially positioning the proximal end 18 of the guidewire 14, or the handle 22 if one is provided. The bead 60 may also be guided along a non-linear path by advancing or retracting the bead 60 relative to the guidewire 14 having a non-linear distal end, as discussed previously. If a marker 90 such as those shown in FIGS. 8A to 8D is provided, it may be used to help determine the orientation of the distal end of the guidewire 14, as discussed previously. Once the bead 60 reaches the target site 150, the bead 60 may be navigated through the target bone tissue to create the desired void.

If the device 10 includes an expandable cutting basket 70, as described previously with reference to FIGS. 7A to 7D, the expandable cutting basket 70 may be advanced distally until it emerges from the distal end 26 of the tubular element 12 and reaches the target bone tissue. The expandable cutting basket 70 is then expanded either manually or by its self-expanding characteristic. Turning the proximal end 18 of the guidewire 14, or the handle 22 if one is provided, then rotates the cutting basket 70. Alternatively, a machine connecting to a proximal end of the cutting basket 70 can be used to rotate the cutting basket 70. The rotation of the cutting basket 70 helps remove target bone tissue at the target site 150, creating the desired void.

If the device 10 includes an electrode at the distal end 16 of the guidewire 14, the electrode may be used to ablate target bone tissue and create a lesion at the target site 150.

Once the void 164 is created, if the size or geometry of the void 164 is not sufficient to cover the entire portion of the target site 150, the delivery device 10 may be oriented to aim at the target site 150 using a different angle 170 selected relative to the axis 154, and the same steps discussed previously may be repeated until a desired geometry and/or size of the void is achieved. (FIG. 14D) In addition, the same steps are preferably repeated on the opposite side of the vertebra 152 in order to create a void 164 that is somewhat symmetric about the axis 171 of the vertebra 152.

Once the void 164 is completely created, the tubular element 12 is then used to deliver a media 172 to the void 164. (FIG. 14E) The media 172 may include granular implants or particles, such as "calcium salts", including ACP, TCP, and $CaSO_4$, $CaPO_4$, Hydroxylapatite (HA), Calcium Aluminate, etc. The media 172 may also include bone cement such as PMMA or the like, and other biomaterials such as donor tissue. The implants or particles or granules within the media 172 may have approximately the same size, or alternatively, may have a distribution of sizes. It should be noted that the type of media 172 being used does not limit the scope of the invention, and that media 172 having other compositions may also be used as long as it is suitable for the particular application. The guidewire 14 may remain within the lumen 30 of the tubular element 12 while the media 172 is being delivered by the tubular element 12. Alternatively, the guidewire 14 may be extracted from the tubular element 12 before delivering the media 172. In either case, the lumen 30 of the tubular element 12 may be used to delivery the media 172. Alternatively, the delivery device 10 may include a second tubular element (not shown) positioned coaxially within the lumen 30 of the tubular element 12 for delivery of the media 172.

If the delivery device 10 includes a vibration device 100, such as that shown in FIG. 9, it may be used to compact the media 172 contained within the void 164. (FIG. 14F) While the distal tip of the guidewire 14 is still within the media 172, the vibration device 100 is activated and causes the guidewire 14 to vibrate. The vibration at the distal end of the guidewire 14 in turn mobilizes the particles or granules within the media 172. In this process, the particles or granules rearrange themselves to mechanically interlock or interdigitate with one another, forming a more stable and tightly knitted structure within the media 172. This results in a media having good consistency and a media that could develop adequate structural strength.

If the delivery device 10 does not include a vibration device, the compaction may be performed by manually tapping the proximal end 18 of the guidewire 14. Alternatively, a separate compaction device such as that shown in FIG. 13 may be used to compact the media 172 within the void 164. In this case, the elongate member 130 of the compaction device 128 is inserted into the lumen 30 of the tubular element 12 and is advanced distally until the distal end of the elongate member 130 emerges from the distal end 26 of the tubular element 12. The distal tip of the elongate member 130 is then positioned so that it is in contact with the media 172. The vibration device 100 is then activated to vibrate the elongate member 130, causing the media 172 to compact.

If it is determined that the compaction is sub-optimal, the compaction process may be reinitiated before the media 172 hardens. In this case, the distal tip of the guidewire 14 or the elongate member 130 of the compaction device 128 (if the delivery device 10 does not have a vibration device 100) may be reintroduced into the media 172 to liquefy and remobilize the media 172 until an optimal fill and distribution are achieved.

Once the media 172 is delivered and/or compacted within the void 164, the guidewire 14 is then retracted proximally until it is completely removed from within the lumen 30 of the tubular element 12. The tubular element 12 is then removed from the channel 162 at the vertebra 154. The media 172 within the void 164 hardens and develops its strength within a period.

In the event that the distal end 16 of the guidewire 14 and/or the drill bead 60 may not be removed from the void 164, the device 10 may further include a safety feature that enables the distal end 16 to be detached from the rest of the guidewire 14. When incorporating such safety feature to the delivery device 10, the distal end of the guidewire 14 and the drill bead 60 are preferably made of a biocompatible material, such as nitinol, so that, when necessary, the guidewire 14 and the drill bead 60 may be left in the bone structure without causing significant harmful effect to the body. Similarly, the distal end of the elongate member 130 of the compaction device 128 shown in FIG. 13 may also be detachably connected to a remainder of the elongate member 130 for safety purposes.

Figure 15A:
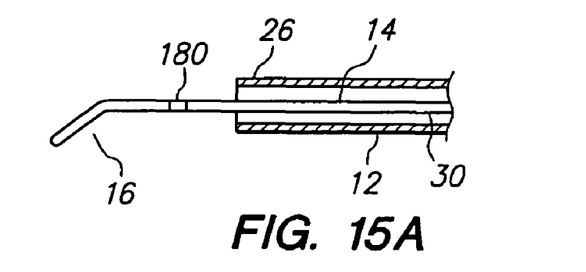
FIG. 15A is a partial cross-sectional side view of the device of FIG. 3, particularly showing the distal end of the guidewire being connected to a proximal portion of the guidewire by a sacrificial link.
Figure 15B:
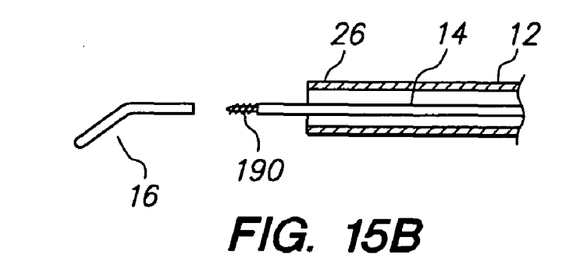
FIG. 15B is a partial cross-sectional side view of the device of FIG. 3, particularly showing the distal end of the guidewire being connected to a proximal portion of the guidewire by a screw-thread.
Figure 15C:
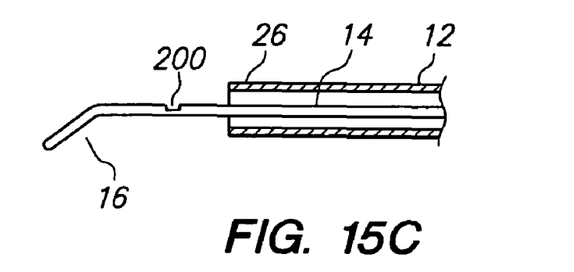
FIG. 15C is a partial cross-sectional side view of the device of FIG. 3, particularly showing a portion of the guidewire removed to create a link.

FIGS. 15A to 15C shows several examples of how the distal end 16 of the guidewire 14 may be severed from the rest of the guidewire 14. FIG. 15A shows a sacrificial link 180 connecting the distal end 16 of the guidewire 14 to the remainder of the guidewire 14, which may be severed by electrolytic activity. Sacrificial links are described in U.S. Pat. No. 6,397,850 B1, and U.S. Pat. No. 6,371,972 B1, the entirety of which is incorporated by reference herein. FIG. 15B shows a mechanism 190 having screw-thread for securing the distal end 16 to the remainder of the guidewire 14. The distal end 16 of the guidewire 14 may be detached by unscrewing the proximal portion of the guidewire 14 from the distal end 16 of the guidewire 14. FIG. 15C shows a link 200 connecting the distal end 16 of the guidewire 14 to the proximal portion of the guidewire 14. The link 200 is a portion of the guidewire 14 that is weakened by removing a portion of the material at the guidewire 14. When it is necessary, the distal end 16 of the guidewire 14 may be severed from the proximal portion of the guidewire 14 by turning and/or pulling the proximal end 18 of the guidewire 14. Due to the inherent weakness at the link 200, the distal end 16 of the guidewire 14 will be severed from the remainder of the guidewire 14 at the link 200. It should be noted that the safety feature of the delivery device 10 is not limited to the examples described previously. Various mechanisms and methods, such as the disconnectable driveshafts described in U.S. Pat. No. 5,766,190, the entirety of which is hereby incorporated by reference, may also be used. Furthermore, various mechanisms and methods for deploying an object within an anatomic void, as are known in the art, may also be used as the safety feature for the delivery device 10.

Although the method of use have been described with reference to treatment of vertebra, it should be noted that the devices described previously may also be used in the treatment of other bone structures, such as the skull, humerus, radius, ulna, femur, fibula, tibia, pelvis, and bones within the hands and feet.

Thus, although several preferred embodiments have been shown and described, it would be apparent to those skilled in the art that many changes and modifications may be made thereunto without the departing from the scope of the invention, which is defined by the following claims and their equivalents.

What is claimed:

1. An apparatus for compacting a media within an anatomic void, comprising:
   a elongate member having a distal end adapted to be positioned within an anatomic void;
   a vibration device connected to a proximal end of the elongate member, wherein the device is configured to vibrate the elongated member for compacting a media within the anatomic void, and wherein the distal end of the elongate member is detachable from a proximal portion of the elongate member by a sacrificial link; and
   a handle coupled to the vibration device, wherein the handle comprises a marker for indicating an orientation of the elongate member.

2. An apparatus for compacting a media within an anatomic void, comprising:
   a elongate member having a distal end adapted to be positioned within an anatomic void;
   a vibration device connected to a proximal end of the elongate member, wherein the device is configured to vibrate the elongated member for compacting a media within the anatomic void, and wherein the distal end of the elongate member is detachable from a proximal portion of the elongate member by a sacrificial link; and
   a tissue ablation electrode carried on the distal end of the elongate member.

3. An apparatus, for compacting a media within an anatomic void, comprising:
- a elongate member having a distal end adapted to be positioned within an anatomic void;
- a vibration device connected to a proximal end of the elongate member, wherein the device is configured to vibrate the elongated member for compacting a media within the anatomic void, and wherein the distal end of the elongate member is detachable from a proximal portion of the elongate member by a sacrificial link; and
- an outer tubular element having a proximal end, a distal end, and a lumen extending there between, the outer tubular element adapted for coaxially surrounding the distal end of the elongate member, wherein the distal end of the elongate member is configured to assume a first profile when the distal end is constrained inside the tubular element, and a second profile when the distal end is unconstrained outside the tubular element.

4. An apparatus for compacting a media within an anatomic void, comprising:
- a elongate member having a distal end adapted to be positioned within an anatomic void;
- a vibration device connected to a proximal end of the elongate member, wherein the device is configured to vibrate the elongated member for compacting a media within the anatomic void, and wherein the distal end of the elongate member is detachable from a proximal portion of the elongate member by a sacrificial link; and
- a removal element coupled to the distal end of the elongate member, the removal element configured for creating an anatomic void within a bone structure, wherein the removal element comprises an expandable structure.

5. An apparatus for compacting a media within an anatomic void, comprising:
- a elongate member having a distal end adapted to be positioned within an anatomic void;
- a vibration device connected to a proximal end of the elongate member, wherein the device is configured to vibrate the elongated member for compacting a media within the anatomic void, and wherein the distal end of the elongate member is detachable from a proximal portion of the elongate member by a sacrificial link; and
- a removal element coupled to the distal end of the elongate member, the removal element configured for creating an anatomic void within a bone structure, wherein the removal element comprises a lesion generator.

6. An apparatus for compacting a media within an anatomic void, comprising:
- a elongate member having a distal end adapted to be positioned within an anatomic void; and
- a vibration device connected to a proximal end of the elongate member, wherein the device is configured to vibrate the elongated member for compacting a media within the anatomic void, and wherein the distal end of the elongate member is detachable from a proximal portion of the elongate member by a sacrificial link, wherein the sacrificial link is configured to be severed by electrolytic activity.

7. An apparatus for compacting a media within an anatomic void, comprising:
- a elongate member having a distal end adapted to be positioned within an anatomic void; and
- a vibration device connected to a proximal end of the elongate member, wherein the device is configured to vibrate the elongated member for compacting a media within the anatomic void, and wherein the distal end of the elongate member is detachable from a proximal portion of the elongate member by a sacrificial link, wherein the elongate member is a guidewire.

8. An apparatus for compacting a media within an anatomic void, comprising:
- a elongate member having a proximal end and a distal end, the distal end adapted to be positioned within an anatomic void;
- a vibration device connected to the proximal end of the elongate member, wherein the device is configured to vibrate the elongated member for compacting a media within the anatomic void, and wherein the distal end of the elongate member is detachable from a proximal portion of the elongate member by a sacrificial link;
- a tissue ablation electrode carried on the distal end of the elongate member; and
- an outer tubular element adapted for coaxially surrounding the distal end of the elongate member.

9. An apparatus for compacting a media within an anatomic void, comprising:
- a elongate member having a proximal end and a distal end, the distal end adapted to be positioned within an anatomic void;
- a vibration device connected to the proximal end of the elongate member, wherein the device is configured to vibrate the elongated member for compacting a media within the anatomic void, and wherein the distal end of the elongate member is detachable from a proximal portion of the elongate member by a sacrificial link;
- an operative element carried on the distal end of the elongate member; and
- an outer tubular element adapted for coaxially surrounding the distal end of the elongate member, wherein the distal end of the elongate member is configured to assume a first profile when the distal end is constrained inside the tubular element, and a second profile when the distal end is unconstrained outside the tubular element.

10. The apparatus of claim 9, wherein the outer tubular element is configured for delivering a media to the anatomic void.

11. The apparatus of claim 9, wherein the outer tubular element is configured for delivering a media from the anatomic void to a biomaterial containment device.

12. The apparatus of claim 9, further comprising an inner tubular element configured for delivery of a media to the anatomic void, the inner tubular element coaxially positioned within the lumen of the outer tubular element.

13. The apparatus of claim 9, wherein the sacrificial link is configured to be severed by electrolytic activity.

14. The apparatus of claim 9, wherein a portion of the distal end of the elongate member is removed to create the sacrificial link.

15. An apparatus for compacting a media within an anatomic void, comprising:
- a elongate member having a proximal end and a distal end, the distal end adapted to be positioned within an anatomic void;
- a vibration device connected to the proximal end of the elongate member, wherein the device is configured to vibrate the elongated member for compacting a media within the anatomic void, and wherein the distal end of the elongate member is detachable by a sacrificial link;
- a handle coupled to the vibration device; and
- a sensor carried on the distal end of the elongate member and capable of measuring a characteristic of the media, wherein the sacrificial link is configured to be severed by electrolytic activity.

* * * * *